United States Patent [19]

Irie

[11] Patent Number: 5,206,270

[45] Date of Patent: Apr. 27, 1993

[54] METHOD OF INHIBITING MELANOMA CELLS

[75] Inventor: Reiko F. Irie, Los Angeles, Calif.

[73] Assignee: Wakunaga Seiyaku Kabushiki Kaisha, Osaka, Japan

[21] Appl. No.: 846,087

[22] Filed: Mar. 5, 1992

[51] Int. Cl.$^5$ ............................................. A61K 31/195
[52] U.S. Cl. ................................................. 514/562
[58] Field of Search ........................................ 514/562

[56] References Cited

U.S. PATENT DOCUMENTS 3,950,542  4/1976  Kalopissis et al. .................. 514/555

OTHER PUBLICATIONS

Chemical Abstracts 106:169054p (1987).
Chemical Abstracts 111:146760e (1989).
Chemical Abstracts 113:126061r (1990).

Primary Examiner—Jerome D. Goldberg
Attorney, Agent, or Firm—Spensley Horn Jubas & Lubitz

[57] ABSTRACT

A method of inhibiting melanoma cell proliferation in a mammal by administering to the mammal S-allylcysteine or a pharmaceutically acceptable salt thereof.

2 Claims, 1 Drawing Sheet

METHOD OF INHIBITING MELANOMA CELLS

BACKGROUND OF THE INVENTION

1. Field of the Invention

This invention relates to the use of S-allylcysteine as an antineoplastic agent. More specifically, it relates to a method of inhibiting the proliferation of certain malignant melanoma cells in a mammal by administering to the mammal the afore-indicated antineoplastic agent.

2. Related Art

Garlic products are believed to possess beneficial effects in maintaining good health such as providing resistance to infections, lowering cholesterol levels, detoxifying harmful substances, relieving stress, and enhancing the immune response. For thousands of years they have been part of folk medicine. Certain extract forms of garlic are antibacterial and antifungal, and others are antithrombotic.

Garlic and onion oils have previously been reported to inhibit carcinogenesis in several experimental animal models (S. Belman, *Carcinogenesis*, 1983, 14, 1063). More specifically, this study reported that garlic and onion oils inhibited the growth of DMBA (7, 12-dimethylbenzenanthracene)-induced or PMA (phorbol-myristate-acetate)-promoted skin papillomas in mice, as well as inhibiting the growth of DMBA-induced hamster buccal pouch carcinomas.

Organosulfur compounds (OSC) isolated from garlic extracts have also been shown to inhibit tumorigenesis induced by chemical carcinogens. For instance, Sumiyoshi et al., in *Cancer Res.*, 1990, 50, 5084, reports that one water soluble OSC (S-allylcysteine) inhibits DMH (1,2-dimethylhydrazine)-induced nuclear aberration in mouse colon. OSC's are believed to stimulate the activity of GST, which is an enzyme known to be involved in the detoxification of many carcinogens. Therefore, increased GST activity may be responsible for the inhibition of tumorigenesis.

These findings, in part, support the conclusions from epidemiologic studies that consumption of fresh fruits and vegetables reduces cancer risk. However, in spite of the apparent chemopreventive effects of garlic extracts and OCS's, prior to the present invention, there was no suggestion that OCS's or its salts could inhibit the proliferation of carcinoma cells.

SUMMARY OF THE INVENTION

The present invention relates to the discovery that S-allylcysteine, or pharmaceutically acceptable salts thereof, inhibit the proliferation of melanoma cells.

In accordance with one aspect of this invention, there is provided an antineoplastic composition comprising a melanoma inhibiting amount of S-allylcysteine and a pharmaceutically acceptable carrier.

This invention is also concerned with a method for the inhibition of melanoma cell proliferation in a mammal, which comprises administering to the mammal, including a human, a melanoma cell inhibiting effective amount of S-allylcysteine or a pharmaceutically acceptable salt thereof.

The objects, features and advantages of this invention will be more fully understood by reference to the following detailed description and drawings.

BRIEF DESCRIPTION OF THE DRAWINGS

In FIG. 1A, O denotes M12 human melanoma cell line; ☐, M14 human melanoma cell line; and Δ, M223 human melanoma cell line.

In FIG. 1B, O denotes M210 human melanoma cell line; ☐, M10 human melanoma cell line; and Δ, M24 human melanoma cell line.

In FIG. 1C, -O- denotes M7 human melanoma cell line; -▲-, M16 human melanoma cell line; -■-, M25 human melanoma cell line; -O-, F10 murine melanoma cell line; and -■-, BL6 murine melanoma cell line.

DETAILED DESCRIPTION OF THE INVENTION

Figure 1A:
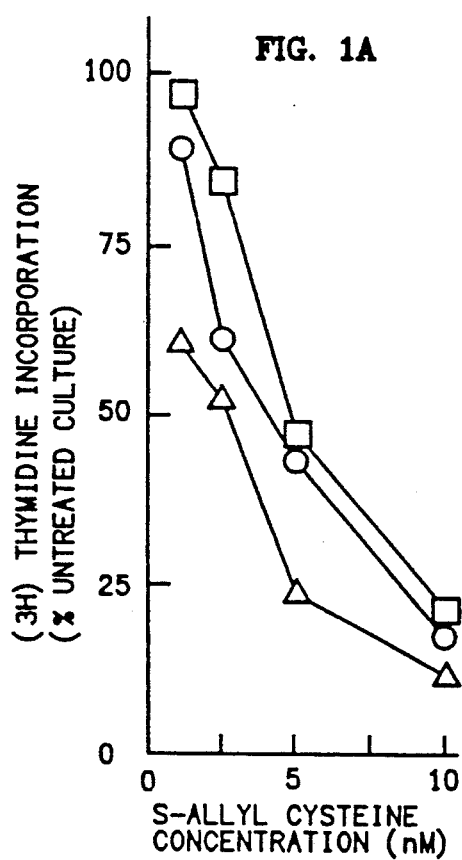
FIGS. 1A, 1B, 1C show effects of S-allylcysteine on [$^3$H]thymidine incorporation in human and murine melanoma cells.

S-allylcysteine can be either chemically synthesized or isolated from garlic extracts, the latter method being disclosed in *Chem. Phar. Bull.*, 1961, 9, 251.

Although the naturally occurring S-allylcysteine is in L-form, the chemically synthesized S-allylcysteine can be in a racemic form, from which the D-form or L-form may be obtained by resolution techniques known to those skilled in the art. Pure L- or D- S-allylcysteine, a partially resolved S-allylcysteine, and a racemic mixture of S-allylcysteine are all within the purview of the present invention.

The present invention also embraces a pharmaceutically acceptable salt of S-allylcysteine such as cationic salts or acid addition salts. Suitable cationic salts include, but are not limited to, the alkali metal salts (e.g., sodium and potassium), alkaline earth metal salts (e.g., calcium and magnesium), aluminum salts, ammonium salts, and salts with organic amines such as benzathine (N,N'-dibenzyl ethylenediamine), choline, diethanolamine, ethylenediamine, meglumine (N-methylglucamine), benethamine (N-benzylphenethylamine), diethylamine, piperazine,tromethamine(2-amino-2-hydroxymethyl-1,3-propanediol),andprocaine.

Pharmaceutically-acceptable cationic salts of S-allylcysteine are readily prepared by reacting the cysteine derovatove with an appropriate base, usually one equivalent, in a reaction-inert solvent. Typical bases are sodium hydroxide, sodium methoxide, sodium ethoxide, sodium hydride, potassium methoxide, magnesium hydroxide, calcium hydroxide, benzathine, choline, diethanolamine, ethylenediamine, meglumine, benethamine, diethylamine, piperazine and tromethamine. The salt is isolated by concentration to dryness or by addition of a non-solvent. In some cases, salts can be prepared by mixing a solution of the acid with a solution of a different salt of the cation (sodium ethylhexanoate, magnesium oleate), employing a solvent in which the desired cationic salt precipitates, or can be otherwise isolated by concentration and addition of a non-solvent.

Suitable acid addition salts include, but are not limited to, hydrochloric acid, sulfuric acid, formic acid, citric acid, trichloroacetic acid, trifluoroacetic acid, methanesulfonic acid, benzenesulfonic acid, p-toluenesulfonic acid, mesytylenesulfonic acid, napthalenesulfonic acid, and the like. The acid addition salts of S-allylcysteine are readily prepared by reacting the cysteine derivative with an appropriate base, usually one equivalent of the appropriate base in a reaction-inert solvent. Those salts which do not precipitate directly are isolated by concentration and/or the addition of a non-solvent.

In the inhibition of a melanoma cell proliferation in a mammal, S-allylcysteine can be administered via oral or parenteral routes. However, it is generally preferred to administer S-allylcysteine or its pharmaceutically acceptable salts orally.

Suitable pharmaceutical compositions, for oral or parenteral administration, can easily be prepared by methods known to those skilled in the art. Such methods and excipients usable can be found in *Remington's Pharmaceutical Sciences* by E. W. Martion (Mark Publ. Co., 15th Ed. 1975).

For purposes of oral administration, tablets containing various excipients such as sodium citrate, calcium carbonate and calcium phosphate may be employed along with various disintegrants such as starch and preferably potato or tapioca starch, alginic acid and certain complex silicates, together with binding agents such as polyvinylpyrrolidone, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection includes the high molecular weight polyethylene glycols. When aqueous suspensions and/or elixirs are desired for oral administration, the essential active ingredients therein may be combined with various sweetening or flavoring agents, coloring matter or dyes, and if so desired, emulsifying and/or suspending agents as well, together with such diluents as water, ethanol, propylene glycol, glycerin and various combinations thereof.

For purposes of parenteral administration, solutions of the active ingredients in sesame or peanut oil or in aqueous propylene glycol or N,N-dimethylformamide may be employed, as well as sterile aqueous solutions of the corresponding water-soluble, non-toxic mineral and organic acid addition salts or alkali or alkaline-earth metal salts previously enumerated. Such aqueous solutions should be suitably buffered, if necessary, and the liquid diluent first rendered isotonic with sufficient saline or glucose. These particular aqueous solutions are especially suitable for intravenous, intramuscular, subcutaneous and intraperitoneal injection purposes. In this connection, the sterile aqueous media employed are readily obtainable by standard techniques well-known to those skilled in the art.

In general, S-allylcysteine or a pharmaceutically acceptable salt thereof is most desirably administered in doses ranging from about 10 mg up to about 1 g, although dose variations may occur depending upon such factors as the weight of the subject being treated, the individual response to the medicament, as well as on the particular type of pharmaceutical formulation chosen and the time period and interval at which administration is carried out. In some instances, dosage levels below the lower limit of the aforesaid range may be more than adequate, while in other cases still larger doses may be employed without causing harmful or deleterious side effects provided that such higher dose levels are first divided into several smaller doses that are to be administered throughout the day.

The activity of S-allylcysteine or pharmaceutically acceptable salts thereof, as antineoplastic agents, is determined by its ability to inhibit the proliferation of an established melanoma cell line.

The present invention is illustrated by the following examples. However, it should be understood that the invention is not limited to the specific details of these examples.

EXAMPLE 1

Cytotoxicity Assay

Chemicals

S-allylcysteine was synthesized according to the method of S. Nakagawa, et al. in Japan Kokai 62-423, disclosed Jan. 6, 1987.

Tumor Cell Lines

Nine human melanoma cell lines (UCLA SO-M7, M10, M12, M14, M16, M24, M25, M210 and M223) were used. Two murine melanoma B16 sublines (F10 and BL6) were also used.

Culture Conditions

All cells were grown in RPMI 1640 medium containing 2 mM glutamine supplemented with 10% fetal bovine serum, gentamicin and fungizone at 37° C. in a humidified atmosphere consisting of 5% $CO_2$ and 95% air.

Exponentially growing cells were inoculated into T-75 flasks (Costar, Pleasanton, Calif.) at a concentration of $1-1.5 \times 10^6$ cells in 15 ml of fresh media. S-allylcysteine at 5 mM was added 24 hours after cell inoculation and re-added at 48 hour intervals to maintain the initial level.

[$^3$H] Thymidine Incorporation and Soft Agar Assay

A standard [$^3$H] thymidine incorporation assay (OS.B. Hoon, et al., *Cancer Res.*, 1987, 47, 1740) was used to evaluate in vitro tumor cell proliferation and growth inhibition of melanoma cells by S-allylcysteine. Ten thousand melanoma cells/well ($10^5$ for lymphocytes and lymphoblasts) were plated in quadruplicate wells for individual tests on a 96-well microplate (Costar). Media was adjusted by varying the S-allylcysteine concentration in each well. The wells were subsequently pulsed with 1 $\mu$Ci[$^3$H] thymidine after 65 hours of incubation. Six hours later the cells were harvested with a PHD harvester (Cambridge Technology, Inc., Cambridge, MA) and counted with a liquid scintillation counter. The ability of tumor cells to form colonies in soft agar in the presence of S-allylcysteine was determined by the method of Tanigawa, et al., *Cancer Res.*, 1982, 42, 2159.

Inhibition of Melanoma Growth by S-allylcysteine

Figure 1B:
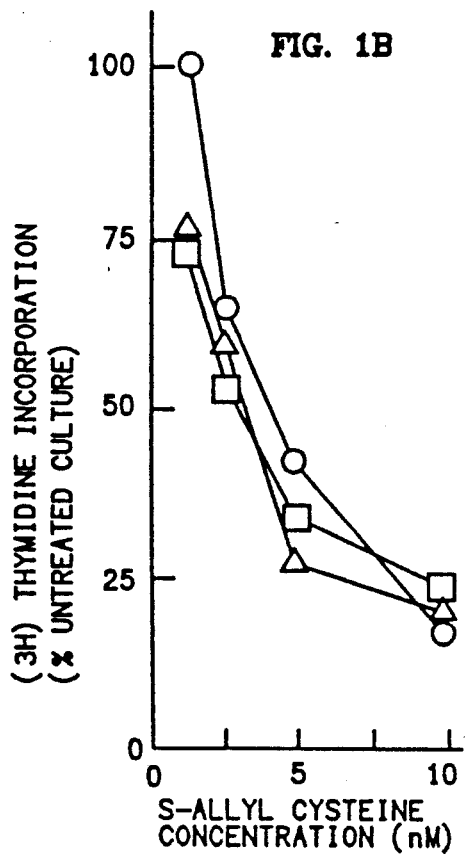
Figure 1C:
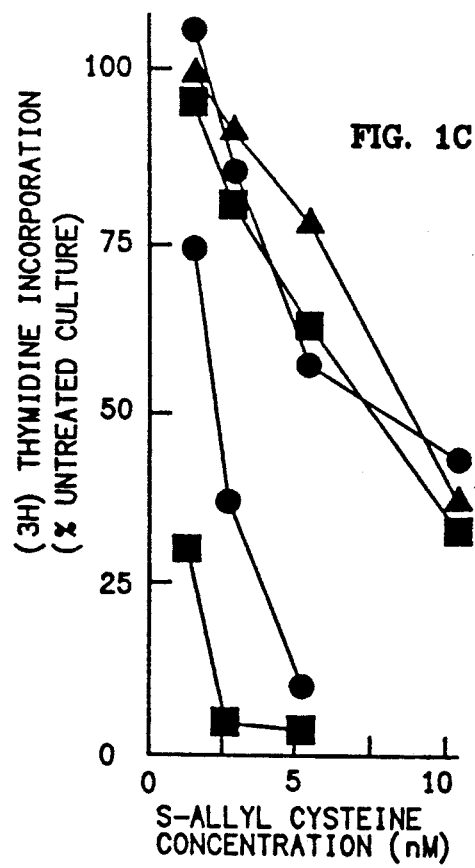

The concentration-dependent effects of S-allylcysteine on cell proliferation measured by the incorporation of [$^3$H]thymidine in nine human melanoma cell lines and two mouse B16 melanoma sublines are shown in FIG. 1. In six of the nine human cell lines, 50-75% inhibition was achieved at an S-allylcysteine concentration of 5 mM, and more than 78% inhibition was achieved in all of the six cell lines (M12, M14, M223, M210, M10, and M24) when the S-allylcysteine concentration reached 10 mM (FIG. 1A,B). The calculated concentrations necessary to inhibit 50% uptake of thymidine are 2.7–4.6 mM, with an average of 3.5 mM ($IC_{50}$). Three cell lines (M7, M16 and M25) were found to be relatively resistant to S-allylcysteine in this system (FIG. 1C). At 5 mM of S-allylcysteine, thymidine incorporation in these cell lines was inhibited an average of 35%. The mean concentration needed for 50% inhibition in these cell lines was 7.3 mM ($IC_{50}$). Mouse B16 melanoma variants (F10 and BL6) were sensitive and exhibited over 90% inhibition of thymidine uptake at 5 mM S-allylcysteine (FIG. 1C).

No significant inhibition was observed in peripheral blood lymphocytes obtained from two melanoma patients. Three human B lymphoblastoid cell lines (L10, L14, L16), autologous to M10, M14 and M16 melanoma cell lines, were transformed by the Epstein-Barr virus [D. F. Iric, et al., *Pro. Natl. Acad. Sci.* U.S.A., 1982, 79, 5666] and used as control cells. All lymphoblastoid cell lines showed an enhancement of thymidine incorporation at S-allylcysteine concentrations of 1.2 and 2.5 mM.

Figure 2:
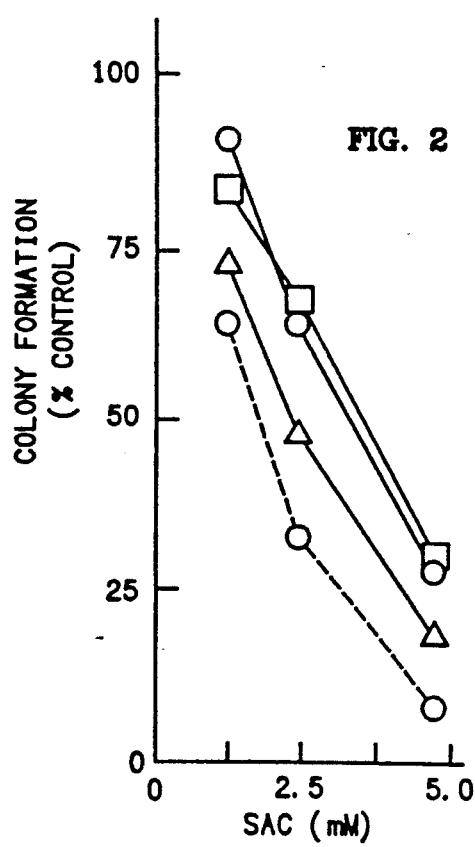
FIG. 2 shows effects of various concentrations of S-allylcysteine (SAC) on colony formation of human melanoma cells. In the figure, -O- denotes M12 human melanoma cell line; ☐, M14 human melanoma cell line; Δ, M223 human melanoma cell line; and -O-, M210 human melanoma cell line.

The effects of S-allylcysteine on the ability of melanoma cells to form colonies in soft agar was also assessed. In this experiment, four human cell lines (M12, M14, M223, M210) were tested. S-allylcysteine inhibited colony formation of all four cell lines in a dose-dependent manner over a range of 1.25 mM-5 mM (FIG. 2). The concentration of S-allylcysteine needed to achieve a 50% suppression varies from 2.7–3.9 mM ($IC_{50}$=3.2 mM) depending on the cell line tested.

The above results indicate that S-allylcysteine inhibited the proliferation of all the melanoma cell lines tested in a dose-dependent manner, whereas the non-malignant cells (peripheral blood lymphocyte and B cell lymphoblastoid cell lines) were not affected by S-allylcysteine.

EXAMPLE 2

Capsules

The following ingredients are combined in the following proportions by weight:

| | |
|---|---|
| S-allylcysteine | 40 |
| Lactose | 200 |
| Cornstarch | 57 |

The mixture is thoroughly blended so as to obtain a uniform powder. Magnesium stearate, sodium lauryl sulfate, 90/10 blend is added and the mixture blended for 30 minutes. The blend is filled into gelatine capsules (50 mg, fill weight) so as to obtain capsules of the desired potency.

EXAMPLE 3

Tablets

The following ingredients are combined in the following proportions by weight:

| | |
|---|---|
| S-allylcysteine | 15 |
| Lactose | 300 |
| Sodium starch glycolate | 15 |
| Hydroxypropyl methycellulose | 5 |
| Magnesium stearate | 5 |

The mixture is thoroughly blended to form a uniform powder. The powder is compressed into tablets containing the desired potency of each active ingredient.

EXAMPLE 4

Injectable Preparation

Sterile sodium salt monohydrate of S-allylcysteine is dry-filled into vials so as to contain 50 mg of the sodium salt dihydrate per vial. Prior to use, sterile water for injection (10 ml) is added, and the mixture shaken to form a solution, containing 5 mg/ml of active ingredient, which is suitable for intravenous, intramuscular or subcutaneous injection.

I claim:

1. A method of inhibiting melanoma cell proliferation in a mammal, which comprises administering to the mammal a melanoma cell inhibiting effective amount of 2-allylcysteine or a pharmaceutically acceptable salt thereof.

2. The method according to claim 1, wherein the S-allylcysteine, or a pharmaceutically acceptable salt thereof, is administered at a concentration from about 10 mg/dose to about 1 g/dose in one or more doses per day.

* * * * *